United States Patent

Wilk

[11] Patent Number: 5,353,785
[45] Date of Patent: * Oct. 11, 1994

[54] METHOD FOR LIFTING ABDOMINAL WALL DURING LAPAROSCOPIC SURGERY

[76] Inventor: Peter J. Wilk, 185 W. End Ave., New York, N.Y. 10023

[*] Notice: The portion of the term of this patent subsequent to Jun. 7, 2011 has been disclaimed.

[21] Appl. No.: 125,652

[22] Filed: Sep. 23, 1993

Related U.S. Application Data

[60] Continuation of Ser. No. 895,018, Jun. 8, 1992, Pat. No. 5,318,012, which is a division of Ser. No. 729,553, Jul. 15, 1991, Pat. No. 5,183,033.

[51] Int. Cl.⁵ .............................................. A61B 17/02
[52] U.S. Cl. ........................................ 128/20; 128/898
[58] Field of Search ........................... 128/20, 8, 898; 606/191, 192, 198, 1, 108; 604/96, 105, 106, 174, 178

[56] References Cited

U.S. PATENT DOCUMENTS

| | | |
|---|---|---|
| 744,204 | 11/1903 | Jordan . |
| 3,517,128 | 6/1970 | Hines . |
| 3,863,639 | 2/1975 | Kleaveland . |
| 4,355,631 | 10/1982 | LeVahn . |
| 4,535,764 | 8/1985 | Ebert . |
| 4,573,452 | 3/1986 | Greenberg . |
| 4,608,965 | 9/1986 | Anspach . |
| 4,834,725 | 5/1989 | Iwatschenko . |
| 4,861,334 | 8/1989 | Nawaz . |
| 4,984,564 | 1/1991 | Yuen . |
| 4,986,810 | 1/1991 | Semrad . |
| 5,002,557 | 3/1991 | Hasson . |
| 5,112,310 | 5/1992 | Grobe . |
| 5,122,122 | 6/1992 | Allgood . |
| 5,188,630 | 2/1993 | Christoudias . |
| 5,197,971 | 3/1993 | Bonutti . |
| 5,217,451 | 6/1993 | Freitas . |

FOREIGN PATENT DOCUMENTS

| | | |
|---|---|---|
| 3837779 | 5/1989 | Fed. Rep. of Germany . |
| 8000034 | 8/1981 | Netherlands . |
| 9218056 | 10/1992 | PCT Int'l Appl. ................. 606/198 |

Primary Examiner—Richard J. Apley
Assistant Examiner—Karen A. Jalbert
Attorney, Agent, or Firm—R. Neil Sudol; Henry D. Coleman

[57] ABSTRACT

A method for use in laparascopic surgery comprises the steps of (a) piercing an abdominal skin surface of a patient to form a hole in the skin surface, (b) inserting through the hole a tensile member, (c) lifting the abdominal wall of the patient away from a backside of the patient by exerting tension on the tensile member, and (d) drawing air into the abdominal cavity of the patient during the step of lifting.

5 Claims, 3 Drawing Sheets

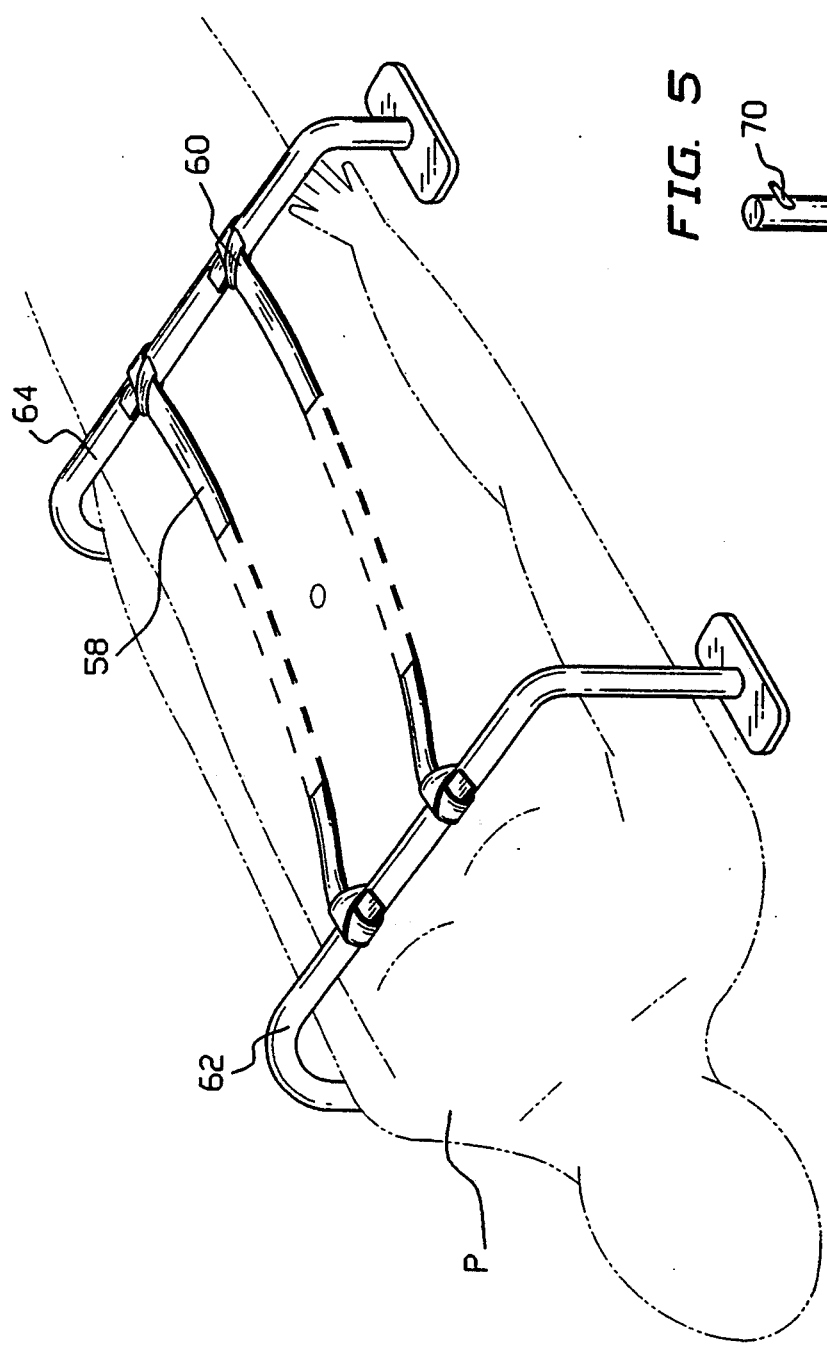
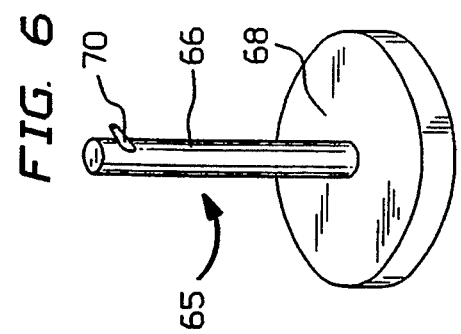
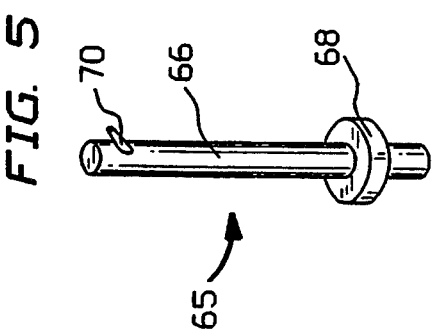

METHOD FOR LIFTING ABDOMINAL WALL DURING LAPAROSCOPIC SURGERY

This is a continuation of application Ser. No. 07/895,018 filed Jun. 8, 1992 now Pat. No. 5,318,012 which is a division of application Ser. No. 729,553 filed Jul. 15, 1991 now Pat. No. 5,183,033.

BACKGROUND OF THE INVENTION

This invention relates to a surgical instrument assembly and apparatus. This invention also relates to an associated surgical method. More particularly, this invention relates to a method, apparatus and instrument for use in laparoscopic surgery.

In conventional laparascopic techniques, a small hollow needle with a safety tip is first inserted through the abdominal wall of a patient. A gas, usually carbon dioxide, is then injected through the needle to pressurize the abdominal cavity and distend the abdominal wall. Surgical instruments are typically introduced into the inflated abdominal cavity through additional apertures formed in the abdominal wall.

Problems with this conventional pneumoperitoneum method include the need for special pumps, pressure gauges and needles and the possiblity of gas seeping into the blood. In addition, the insufflation gas periodically seeps out of the abdominal cavity, whereupon the abdominal wall falls and interrupts the surgery.

OBJECTS OF THE INVENTION

An object of the present invention is to provide an improved method for use in laparoscopic surgery.

Another object of the present invention is to provide associated apparatus and instrumentation for performing the improved method.

Another, more particular, object of the present invention is to provide such a method which would eliminate the need for special equipment.

A further particular object of the present invention is to provide such a method which would prevent collapse of the abdominal wall and loss of pneumoperitoneum.

A related object of the present invention is to provide a method which would allow the use of regular surgical instruments in a patient's abdomen during a laparoscopic procedure.

Yet another particular object of the present invention is to provide such a method which would facilitate smoke evacuation from a distended abdomen during a laparoscopic procedure.

SUMMARY OF THE INVENTION

A method for use in laparascopic surgery comprises, in accordance with the present invention, the steps of (a) piercing an abdominal skin surface of a patient to form a hole in the skin surface, (b) inserting through the hole a tensile member, (c) lifting the abdominal wall of the patient away from a backside of the patient by exerting tension on the tensile member, and (d) drawing air into the abdominal cavity of the patient during the step of lifting.

Preferably, an extra-abdominal channel is formed in the abdominal wall of the patient. The hole defines one end of the channel. In that event, the step of piercing includes the step of inserting a long needle-like instrument through abdominal tissues in a direction substantially parallel to the skin surface to form the channel.

Pursuant to another feature of the present invention, the tensile member is a flexible member such as a tape. Alternatively, the tensile member may take the form of a rigid member such as a tube which carries an expandable member for engaging, in an opened configuration, an enlarged area of the abdominal wall of the patient. The expandable member may include, for example, an inflatable balloon member or a folding linkage. The expandable member is insertable in a collapsed or closed configuration through the hole formed in the patient's abdominal wall. Upon insertion into the patient's abdominal cavity, the expandable member is expanded from the closed configuration to the expanded or opened configuration, whereby a substantially portion of the interior side of the abdominal wall may be engaged and moved by exerting the tension on the rigid tensile member.

Pursuant to another feature of the present invention, the abdominal wall of the patient is maintained in a predetermined elevation upon attainment of the elevation during the step of lifting the patient's abdominal wall. The elevation maintenance may be implemented by holding the tensile member in a predetermined position. More particularly, the tensile member or an extension may be tied to a support. Alternatively, a tensioning element, such as a winch, to which the tensile element is connected may be locked.

An apparatus for use in laparoscopic surgery comprises, in accordance with the present invention, a tensile member engageable with a portion of an abdominal wall of a patient and means disposed outside of the patient and connected to the tensile member for maintaining the tensile member in a predetermined position, thereby maintaining a desired elevational of the abdominal wall of the patient during a laparoscopic procedure.

The elevation maintenance component may include a support, the tensile member being tied to the support. More specifically, the support may take the form of a bar extending above the patient.

Alternatively or additionaly, the tensile member may be tied to a winch which in turn is mounted to the support.

An instrument for use in laparoscopic surgery comprises, in accordance with the present invention, a tubular element insertable through an abdominal wall of a patient and means expandable from a closed configuration to an opened configuration for engaging, in the opened configuration, an enlarged area of the abdominal wall of the patient.

The wall engaging component may include an inflatable balloon member or a folding linkage.

A method in accordance with the present invention eliminates the need for special equipment such as pumps and pressure gauges. This method also prevents collapse of the abdominal wall. Regular surgical instruments may be utilized in a patient's abdomen during a laparoscopic procedure incorporating the instant invention. In addition, a laparoscopic method in accordance with the present invention facilitates smoke evacuation from a distended abdomen.

BRIEF DESCRIPTION OF THE DRAWING

FIG. 4 is a schematic perspective view of a patient at an operative stage similar to that shown in FIG. 3, illustrating a different apparatus in accordance with the present invention.

FIG. 5 is a perspective view of an instrument for use in laparoscopic surgery, in accordance with the present invention, showing the instrument in a closed, pre-use or post use configuration.

FIG. 6 is a perspective view of the instrument of FIG. 5, depicting the instrument in an opened use configuration.

DETAILED DESCRIPTION

Figure 1:
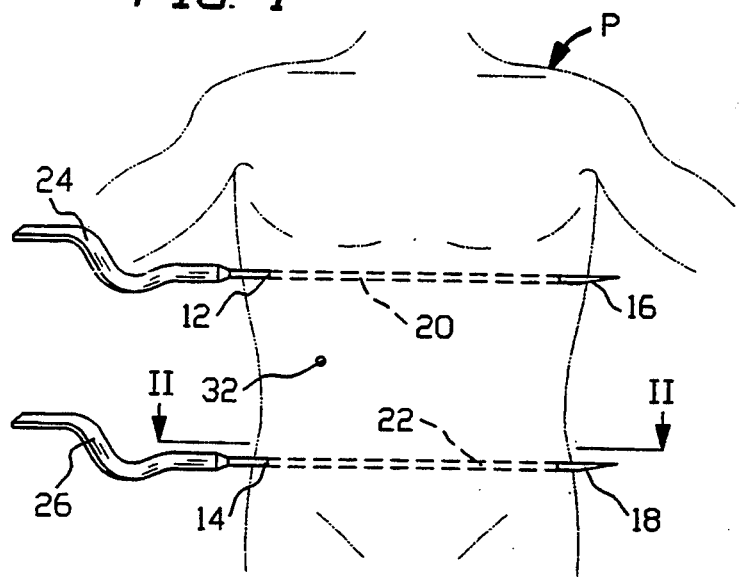
FIG. 1 is a schematic top view of a patient during an initial stage of a laparoscopic procedure in accordance with the present invention.
Figure 2:
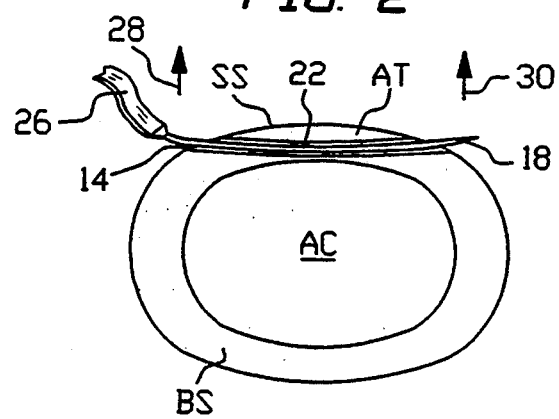
FIG. 2 is a schematic cross-sectional view of the abdomen of the patient of FIG. 1, taken along line II—II in that drawing figure.

As illustrated in FIGS. 1 and 2, a laparoscopic procedure is initiated by piercing the abdominal skin of a patient P at one or more locations 12 and 14 to form holes at those locations. The piercing step is implemented with one or more long, sturdy needles 16 and 18. As shown particularly in FIG. 2, needles 16 and 18 are inserted through abdominal tissues AT in a direction substantially parallel to the skin surface SS to form extra-abdominal channels 20 and 22 in the abdominal wall AW of the patient P. Thus, the holes at piercing locations 12 and 14 define one end of the respective channels 20 and 22.

Attached to proximal ends of needles 16 and 18 are respective tensile members in the form of tapes or ribbons 24 and 26. Needles 16 and 18 are pulled at their free ends until tapes traverse channels 20 and 22 from one end to the other. Tapes 24 and 26 are then pulled upwardly at each end, as indicated by arrows 28 and 30 in FIG. 2, so that abdominal wall AW is lifted away from a back side BS of patient P.

During the lifting of abdominal wall AW by tapes 24 and 26, air is sucked into abdominal cavity AC of patient P via an aperture 32 (FIG. 1) formed in abdominal wall AW by a trocar (not illustrated).

Figure 3:
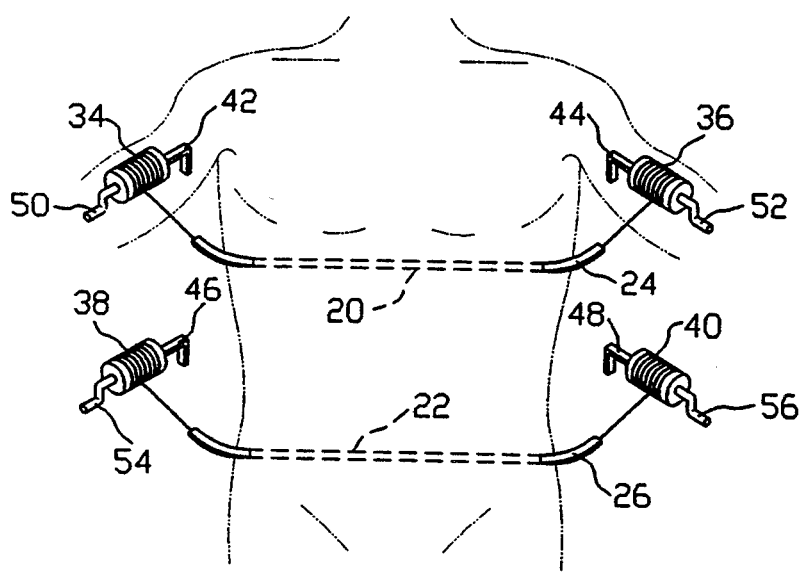
FIG. 3 is schematic top view of a patient and apparatus in accordance with the present invention during a later stage of a laparoscopic procedure in accordance with the invention.

As illustrated in FIG. 3, tapes 24 and 26 may be connected at their opposite ends to respective pairs of winches 34, 36 and 38, 40 or other mechanisms for placing the tapes in tension to facilitate the abdomen lifting operation. Winches 34, 36 and 38, 40 are connected to supporting structures, as schematically indicated at 42, 44 and 46, 48. Winches 34, 36 and 38, 40 may be provided with handles 50, 52 and 54, 56 for facilitating a manual tensioning of tapes 24 and 26. Alternatively, the tensioning may be accomplished automatically through electrical motors or other mechanisms (not illustrated). In addition, winches 34, 36 and 38, 40 may be provided with locks (not shown) for maintaining tapes 24 and 26 at predetermined positions and tensions, thereby maintaining a predetermine elevation of abdominal wall AW with respect to back side BS.

Tapes 24 and 26 may, of course, be inserted intra-abdominally instead of extra-abdominally. In that event, the tapes engage an inner surface of abdominal wall AW.

As depicted in FIG. 4, tapes 58 and 60 may be inserted in directions longitudinally oriented with respect to patient P, rather than transversely, as shown in FIGS. 1–3. The ends of tapes 58 and 60 are tied to a pair of U-shaped bars 62 and 64 which extend in part transversely over patient P. Of course, winches, levers, or any other tightening mechanism may be used to connect tapes 58 and 60 to bars 62 and 64.

FIGS. 5 and 6 show an instrument 65 for use in performing an abdominal lifting technique as described herein. The instrument includes a tube 66 provided at a distal end with an expandable ballon member 68. FIG. 5 shows the ballon member 68 in a closed, pre-use or post-use configuration, while FIG. 6 shows the ballon member in an expanded or opened use configuration. At a proximal end, tube 66 is formed with an inlet 70 couplable with a hose of a pressurized air supply (not shown), whereby balloon member 68 may be inflated from the closed configuration of FIG. 5 to the expanded configuration of FIG. 6.

Upon insertion of the distal end of instrument 65 into a patient's abdominal cavity through his or her abdominal wall, balloon member 68 is inflated to form the expanded configuration of FIG. 6. In the expanded configuration, balloon member 68 can engage a large area on the inside surface of the patient's abdominal wall, thereby facilitating a lifting of the wall from the back side of the patient. Tube 66 functions during a lifting operation as a tensile member.

It is to be noted that balloon member 68 need not take the disk shape of FIG. 6 but may instead have virtually any shape in its opened configuration. Examples include a rectangle, a cross, a hemisphere, a star, etc.

Figure 7:
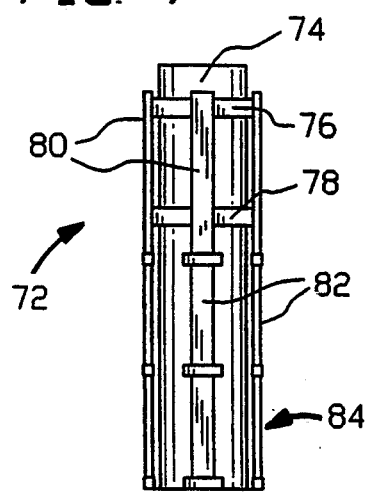
FIG. 7 is a perspective view of another instrument for use in laparoscopic surgery, in accordance with the present invention, showing the instrument in a closed, pre-use or post use configuration.
Figure 8:
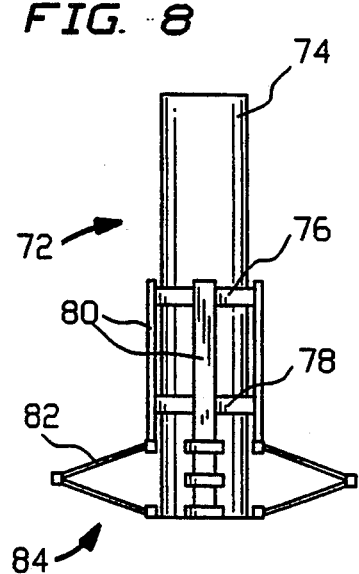
FIG. 8 is a perspective view of the instrument of FIG. 7, depicting the instrument in an opened use configuration.

FIGS. 7 and 8 show another instrument 72 for use in performing an abdominal lifting technique as described herein. The instrument includes a carrier tube or bar 74. A pair of collars 76 and 78 are slidably mounted to tube 74 at a proximal end thereof. Attached to collars 76 and 78 are a plurality of longitudinally extending fingers 80 connected at their distal ends to hinged members 82. Hinged members 82 define an expandable member 84 shown in a closed, pre-use or post-use configuration in FIG. 7 and an expanded or opened use configuration in FIG. 8. Upon insertion of the distal end of instrument 72 into a patient's abdominal cavity through his or her abdominal wall, collars 76 and 78, together with fingers 80 are shifted in the distal direction so that expandable member 84 assumes its expanded or opened configuration (FIG. 8). In that opened configuration, expanded member 84 can engage a large area on the inside surface of the patient's abdominal wall, thereby facilitating a lifting of the wall from the back side of the patient. Tube 74 functions during a lifting operation as a tensile member.

It is to be noted that the instrument 72 of FIGS. 7 and 8 may be modified in numerous ways without departing from the spirit of the invention. For example, fingers 80 and collars 76 and 78 may be replaced by a single sleeve to which hinged members 82 are pivotably attached.

Figure 9:
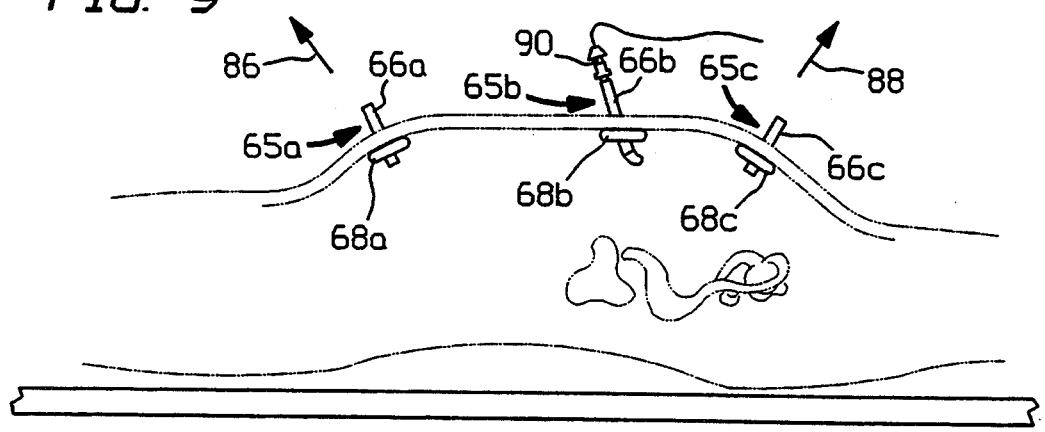
FIG. 9 is a schematic longitudinal cross-sectional view of a patient during an operative stage of a laparoscopic procedure utilizing a method in accordance with the present invention.

FIG. 9 illustrates the use of instruments 65 (or 72) to perform a laparoscopic surgical procedure. A plurality of instruments 65a, 65b and 65c are inserted through an abdominal wall AW' of a patient P' and balloons 68a, 68b and 68c are inflated to their fully opened or expanded configurations. Tubes 66a, 66b, and 66c are then pulled upwardly (and perhaps outwardly, as indicated by arrows 86 and 88. One or more tubes 66b may be traversed by endoscopic or surgical instruments 90.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A method for use in laparascopic surgery to expand an abdominal cavity without positively pressurizing that cavity, comprising the steps of:

piercing an abdominal skin surface of a patient to form a plurality of spaced holes in said skin surface;

inserting through said holes respective tensile members;

lifting the abdominal wall of said patient away from a backside of said patient by exerting tension on said tensile members;

drawing air into the abdominal cavity of said patient during said step of lifting;

inserting a laparoscopic instrument through at least one of said holes so that a distal end of said instrument projects into the patient's abdomen;

maintaining tension on said tensile members, and thereby a predetermined elevation of the abdominal wall of said patient, during the insertion of said instrument through said one of said holes and during a subsequent surgical operation by said laparoscopic instrument; and maintaining the patient's abdomen at essentially atmospheric pressure during said surgical operation.

2. The method recited in claim 1 wherein at least one of said tensile members is a rigid member.

3. The method recited in claim 2 wherein said rigid member is provided with means expandable from a closed configuration to an opened configuration for engaging, in said opened configuration, an enlarged area of the abdominal wall of said patient.

4. The method recited in claim 3 wherein said means for engaging includes an inflatable balloon member.

5. The method recited in claim 3 wherein said means for engaging includes a folding linkage.

* * * * *